US007309601B2

(12) United States Patent
Pérez Esteban et al.

(10) Patent No.: US 7,309,601 B2
(45) Date of Patent: Dec. 18, 2007

(54) SEQUENCES FROM AN ENDOSYMBIONT AND THEIR USES

(75) Inventors: Beatriz Pérez Esteban, Madrid (ES); Tomás Aparicio Pèrez, Madrid (ES); Ana Velasco Iglesias, Madrid (ES); Rubén Henriquez Peláez, Madrid (ES); Rosario Muñoz Moreno, Madrid (ES); Claire Moss, Argyll (GB); Douglas McKenzie, Argyll (GB)

(73) Assignee: Pharma Mar, S.A.U., Madrid (ES)

( * ) Notice: Subject to any disclaimer, the term of this patent is extended or adjusted under 35 U.S.C. 154(b) by 0 days.

(21) Appl. No.: 10/524,152

(22) PCT Filed: Aug. 13, 2003

(86) PCT No.: PCT/GB03/03538

§ 371 (c)(1), (2), (4) Date: Aug. 24, 2005

(87) PCT Pub. No.: WO2004/015143

PCT Pub. Date: Feb. 19, 2004

(65) Prior Publication Data

US 2006/0167228 A1    Jul. 27, 2006

(30) Foreign Application Priority Data

Aug. 13, 2002    (GB)    ................. 0218813.4

(51) Int. Cl.
| | |
|---|---|
| *C12N 1/20* | (2006.01) |
| *C12N 1/14* | (2006.01) |
| *C12Q 1/68* | (2006.01) |
| *C07H 21/04* | (2006.01) |

(52) U.S. Cl. ................ 435/252.3; 435/6; 435/255.4; 536/23.1

(58) Field of Classification Search ............... 536/23.1; 435/6, 253.2, 252.3, 255.4
See application file for complete search history.

(56) References Cited

U.S. PATENT DOCUMENTS 5,976,791 A * 11/1999 Mabilat et al. ................ 435/6

OTHER PUBLICATIONS

Moss et al., Database GenEmbl, Accession No. AY054370, Aug. 2001.*
Moss et al., "Intracellular bacteria associated with the acoidian *Ecteinascidia turbinata*: phylogenetic and in situ hybridisation analysis," Marine Biology, (2003) vol. 143, pp. 99-110, published online Mar. 29, 2003.

* cited by examiner

*Primary Examiner*—Maryam Monshipouri
(74) *Attorney, Agent, or Firm*—Kenneth H. Sonnenfeld; Michael A. Willis; King & Spalding, LLP

(57) ABSTRACT rDNA corresponding to an endosymbiotic bacteria associated with *Ecteinascidia turbinata* has been identified. The bacterium appears to be responsible for the biosynthesis of ecteinascidin compounds. The 16S rDNA sequence corresponding to *Candidatus* Endoecteinascidia frumentensis SEQ ID NO: 1 has been deposited in GeneBank with the accession number AY054370.

5 Claims, 7 Drawing Sheets

SEQUENCES FROM AN ENDOSYMBIONT AND THEIR USES

This application is the National Phase entry of PCT/GB03/03538 filed Aug. 13, 2003, which claims priority to British Patent Application 0218813.4, filed Aug. 13, 2002.

FIELD OF THE INVENTION

The present invention relates to polynucleotide sequences isolated from a bacterial endosymbiont of the ascidian *Ecteinascidia turbinata*, microorganisms containing them and their use in the production of ecteinascidin compounds. The present invention further relates to polypeptides or proteins encoded by said polynucleotide sequences and their use in the production of ecteinascidin compounds.

BACKGROUND TO THE INVENTION

The ascidian, *Ecteinascidia turbinata*, is a colonial tunicate from the family Perophoridae, found in the Caribbean and Mediterranean Seas. As an important component of the benthic ecology of the Caribbean mangroves, it has been the subject of various studies examining settlement, species succession and larval behaviour.

In the 1960's interest in this species was heightened when an extract of the animal was found to have cytotoxic properties. It was not until the 1980's that the compounds conferring these properties, the ecteinascidins, were identified and characterised. One of these compounds, ET-743, with remarkable cytotoxic acitvity, is presently in clinical trials for the treament of cancer.

Nearly 20 years on, little is known about the production of these important secondary metabolites or what function, if any, they play in the animal.

Bioactive secondary metabolites are found in many marine invertebrates; especially sponges, molluscs, bryozoans and ascidians, and new compounds are constantly being described.

Marine invertebrate secondary metabolites encompass a wide range of chemical types including macrolides, terpenes, steroids, peptides and alkaloids, frequently with complex structures. As yet, there is little direct evidence for the function these compounds may have in their hosts, although relevant laboratory and field-based studies are beginning to address this area. Some investigations support a role in chemical defense, as anti-fouling, anti-infective or anti-predation agents. Many sponges are known to produce noxious chemicals and feeding studies have indicated that these compounds appear to confer protection against predators. Marine larvae of chemically defended adults also possess anti-predatory compounds.

As soft bodied, sessile marine invertebrates, adult ascidians are especially susceptible to predation, and to fouling of their external surfaces. The production of potentially defensive secondary metabolites appears widespread among certain groups of ascidians. Feeding studies using crab and fish predators have indicated that in some ascidians these metabolites confer antipredatory protection. Many ascidians also produce large, conspicuous larvae, which develop in a brood pouch. These larvae are released in daylight hours, so they can search for optimal settlement sites, and have a short swimming phase. This strategy leaves the larvae exposed to predators and it has been suggested that selection by these predators may favour the evolution of distasteful larvae. Indeed many such larvae may be chemically defended, being unpalatable to predators when presented in feeding experiments.

There is little known of the mechanisms of production of secondary metabolites in many species. There is evidence to support the theory that symbionts (especially bacterial ones) within the invertebrate host produce at least some of these secondary metabolites, either on their own, or in conjunction with their host. This idea is based on the fact that some secondary metabolites show close similarities to compounds produced by bacteria. Although the evidence to support this theory is still limited, and in some cases the picture is likely to be very complex with no clear unique source for a metabolite, certain studies have added experimental support to the argument.

Although there are many secondary metabolite-producing ascidians, there are very few studies on the presence of microorganisms specifically associated with ascidians, as epi- or endobionts. However, there are now many descriptions of symbiotic associations between bacteria and other marine invertebrate hosts, for example in sponges, molluscs, bryozoans and echinoderms.

Despite the increasing number of studies, the association between chemical defense, secondary metabolites and bacterial symbiosis, is not understood.

*Ecteinascidia turbinata* is the source of natural product ET-743 which is being developed as antitumoral agent. The cytotoxic compound is extracted from the ascidian which is obtained by aquaculture. Due to the life cycle of the *Ecteinascidia turbinata* this is a time consuming and laborious process.

Chemical routes to ET-743 are the total synthesis, and the hemisynthesis from cyanosafracin B obtained by fermentation. Although these processes provide alternatives to the natural sources of ecteinascidins, they still involve numerous chemical steps and are expensive.

There is a need to provide new sources of the ecteinascidin compounds which are not subject to the difficulties described above.

SUMMARY OF THE INVENTION

The present invention is directed to a DNA sequence as defined by SEQ ID NO: 1 below or fragments (parts) thereof.

```
SEQ ID NO: 1
ATGAATTCTGGTGGCACTGCTTAACACATGCAAGTCGAACGGTAACATAA

TAAATGTTTTTTACATTTATGGATGACGAGTGGCGGACGGGTGAGTAACG

CGTAGGAACCTACCTTTTAGTGGGGATAGCAGTGGGAAACTACTGGTAA

TACCGCATGATACTTTAGAGTTAAAACTAGCTGAATTTTATAGCTTGTGC

TAAAAGACGGGCCTGCGTTAGATTAGCTTGTTGGTAAGGTAACGGCTTAC

CAAGGCAACGATCTATAGCTGTTCTGAGAGGAAGATCAGCCACACTGGGA

CTGAGATACGGCCCAGACTCCTACGGGAGGCAGCAGTGGGGAATATTGGA

CAATGGGCGGAAGCCTGATCCAGCAATGCCACGTGTGTGAAGAAGGCCTT

CGGGTTGTAAAGCACTTTTATTAGCGAAGAAGATATAATGGTTAAGAGCT

TAATATATTTGACGTTAGCTAAAGAAAAAGCACCGGCTAACTCCGTGCCA

GCAGCCGCGGTAATACGGAGGGTGCAAGCGTTAATCGGAATTATTGGGCG

TAAAGAGCCTGTAGGTGGATAATTAAGTCAGATGTGAAATCCCAAAGCTT

AACTTTGGAACTGCATTTGAAACTAATTATCTAGAGTATAGTAGAGGGTA
```

-continued

```
GAGGAATTTCCGGTGTAGCGGTGAAATGCGTAGAGATCGGAAGGAACATC

AGTGGCGAAGGCGTCTACCTGGGACTAAAACTGACACTGAGAGGCGAAAG

CATGGGGAGCAAACAGGATTAGATACCCTGGTAGTCCATGCCGTAAACTA

TGAGTACTAACTGTTGGAATTTTTAAATTTTAGTAGTGGAGCTAACGCAA

TAAGTACTCCGCCTGGGGATTACGGCCGCAAGGCTAAAACTCAAAGGAAT

TGACGGGGGCCCGCACAAGCGGTGGAGCATGTGGTTTAATTCGATGCAAC

GCGAAAAACCTTACCTACTCTTGAAATCCTTCGTACTTTATAGAGATATA

AAGGTGCCTTTGGAACGAAGTGACAGGTGCTGCATGGCTGTCGTCAGCTC

GTGTCGTGAGATGTTGGGTTAAGTCCCGTAACGAGCGCAACCCTTTCCCT

TAGTTGCCAGCGTGTAAAGACGGGGACTCTGAGGGGACTGCCGGTGATAA

ACCGGAGGAAGGCGAGGACGACGTCAAGTCATCATGGTCCTTACGAGTAG

GGCTACACACGTGCTACAATGGTATGTACAAAGGGAGGCAAAATTGTAAA

ATCTAGCAAATCCCCAAAAGCATATCTTAGTCCGGATTGAAGTCTGCAAC

TCGACTTCATGAAGTTGGAATCGCTAGTAATCGCGAATCAGCATGTCGCG

GTGAATACGTTCCCGGGCCTTGTACACACCGCCCGTCACACCACGGAAGT

GGAATGCACCAGAAGTGGCTAGGATAACCGAAAGGAGTCCGGTCCCTACG

GTGTGTTTCGTAACTGGGGTGAAGTCGTAACAAGGTAGCCGTAGGGAACT

GC
```

Fragments (parts) of the sequence suitably have a length of at least 5, 10, 15, 20, 25, 30 or more nucleotide residues. The invention also embraces modifications or variations in the sequence SEQ ID 1, including deletions, insertions, replacements and other changes. Such modified or varied sequences typically have at least 50%, 70%, 75%, 85%, 90%, 95% or 97% homology with SEQ ID NO:1. References in the following description to the SEQ ID NO: 1 or fragments (parts) thereof include such modifications or variations.

In another aspect, the present invention relates to the use of the DNA sequence SEQ ID 1, or parts thereof, in an assay to identify nucleic acid molecules involved in the biosynthesis of ecteinascidin compounds, particularly by walking chromosome techniques.

The present invention is also directed to (a) polynucleotide sequences isolated from *Ecteinascidia turbinata* in any of its development phases, its dissociated cells or cultures thereof, and/or a microorganism associated therewith, involved in the biosynthesis of ecteinascidin compounds, identified with an assay as defined above using the sequence SEQ ID NO: 1 or parts thereof.

The invention is also directed to (b) a sequence which is able to hybridize, under stringent conditions, with a molecule according to (a), or fragments (parts) thereof. Suitable conditions for such hybridisation are given in the examples, at 45° C. for 3 hours in buffer (0.9M NaCl, 20 mM Tris-HCl pH 7.2, 1× Denhardts, 0.1% SDS, 5 mM EDTA, 0.1 mg/ml Poly(A)) with 2.5 ng/μl of probe which had been reconstituted in TE.

The invention is also directed to sequences which, because of the degeneracy of the genetic code, differ from the molecules according to (a) and (b), or parts thereof.

A polynucleotide, modification, variant or fragment of the invention may be single stranded or double stranded and may be DNA, RNA or a DNA/RNA hybrid.

In another aspect the present invention relates to polypeptides or proteins encoded by the DNA or other polynucleotide molecules as defined above.

A modified or variant polypeptide suitably has at least one biological function of the non-modified or non-variant polypeptide or protein. It is preferred that modification or variation of a polypeptide or protein of the invention is such that a biological function of the polypeptide or protein, in particular a function relating to biosynthesis of an ecteinascidin compound, precursor, intermediate, or a compound involved in biosynthesis thereof, is modulated, maintained or improved.

The term polypeptide is interchangeable with protein. A polypeptide or protein and a modified or variant polypeptide or protein are structurally related in terms of amino acid composition and sequence. Structurally related polypeptides have at least 60%, preferably at least 70%, more preferably at least 80%, yet more preferably at least 90%, further preferably at least 95% amino acid sequence homology. A modified or variant polypeptide or protein may be chemically modified or may have one or more amino acid as substitution, deletion and/or addition. Preferably 1 to 20, 1 to 16, 1 to 12, or 1 to 10 amino acids are substituted, deleted and/or added; most preferably 1, 2, 3, 4, 5, or 6 amino acids are substituted, deleted and/or added. Preferably, the modification of the polypeptide is by amino acid substitution, which can be substitution of one or more amino acids, preferably by substitution of 1 to 20, 1 to 16, 1 to 12, or 1 to 10 amino acids, more preferably substitution of 1, 2, 3, 4, 5, or 6 amino acids. Alternatively, modification of the polypeptide may be by deletion of one or more amino acids, preferably by deletion of 1 to 20, 1 to 16, 1 to 12, or 1 to 10 amino acids; more preferably by deletion of 1' 2, 3, 4, 5, or 6 amino acids.

In another aspect the present invention is also directed to a microorganism comprising a sequence according to SEQ ID NO: 1 or parts thereof. More particularly the microorganism is a bacterium.

In another aspect, the invention is directed to the use of a microorganism as defined above in the production of an ecteinascidin compound, a precursor or intermediate thereof, or a compound involved in the biosynthesis of ecteinascidin compounds.

The invention furthermore relates to a (host) cell comprising any one of the above-described DNA molecules, in particular a (host) cell which is transformed or transfected with any one of the above-described DNA molecules.

In another aspect the invention relates to a process for the amplification of a DNA molecule which is as described above, preferably amplification is by PCR amplification.

The invention furthermore relates to a process for investigating the gene cluster for biosynthesizing ecteinascidin compounds, characterized in that:
a) hybridization probes which are derived from the DNA sequence as defined by SEQ ID NO: 1 are prepared and
b) these hybridization probes are used for the genomic screening of DNA libraries obtained from *Ecteinascidia turbinata,* and
c) the clones which are found are isolated and characterized.

Figure 1:
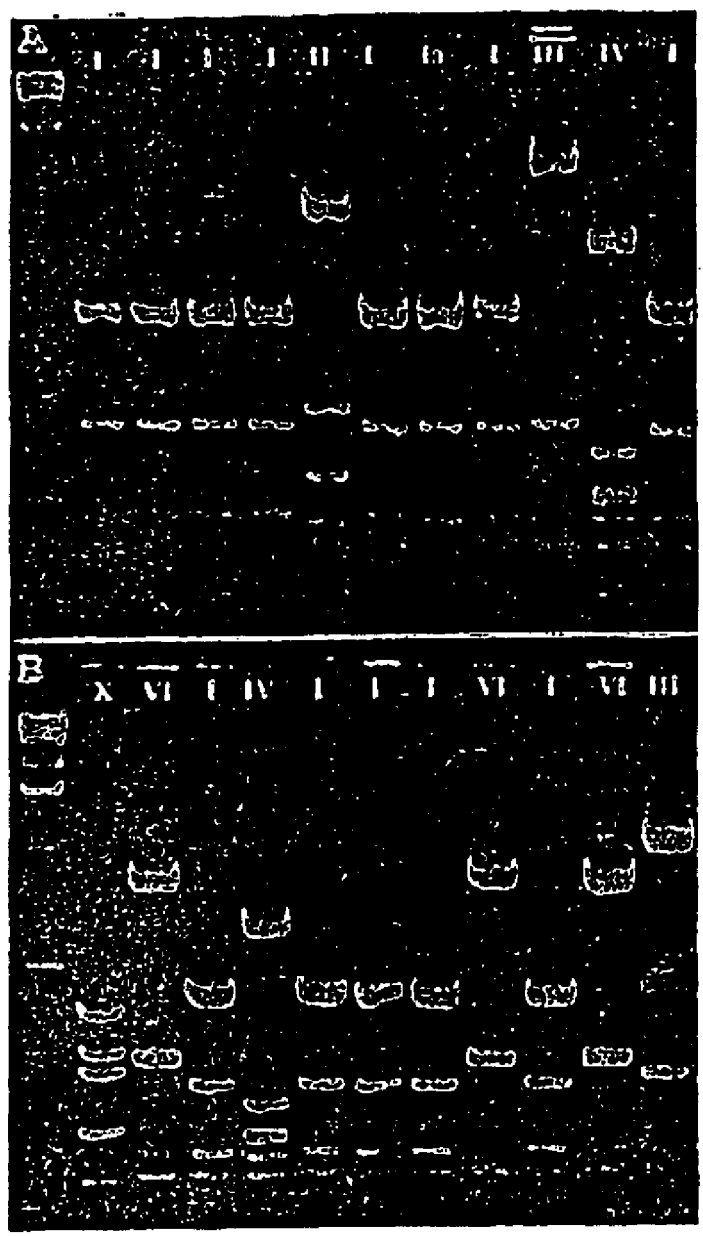
FIG. 1. RFLP analysis of clone inserts. HaeIII digests of 16S rDNA insert. In both cases Lane 1=DNA marker.

A. RFLP's from larval material showing the common Type 1 (lanes 2-5, 7, 9, 12), III (lane 10) and IV (lane 11) RFLP pattern.

B. RFLP's from stolon material showing the Type I (lanes 4, 6-8, 10), III (lane 12), IV (lane 5) and VI (lanes 3, 9, 11) patterns. Other patterns observed are indicated by Roman numerals.

Figure 2:
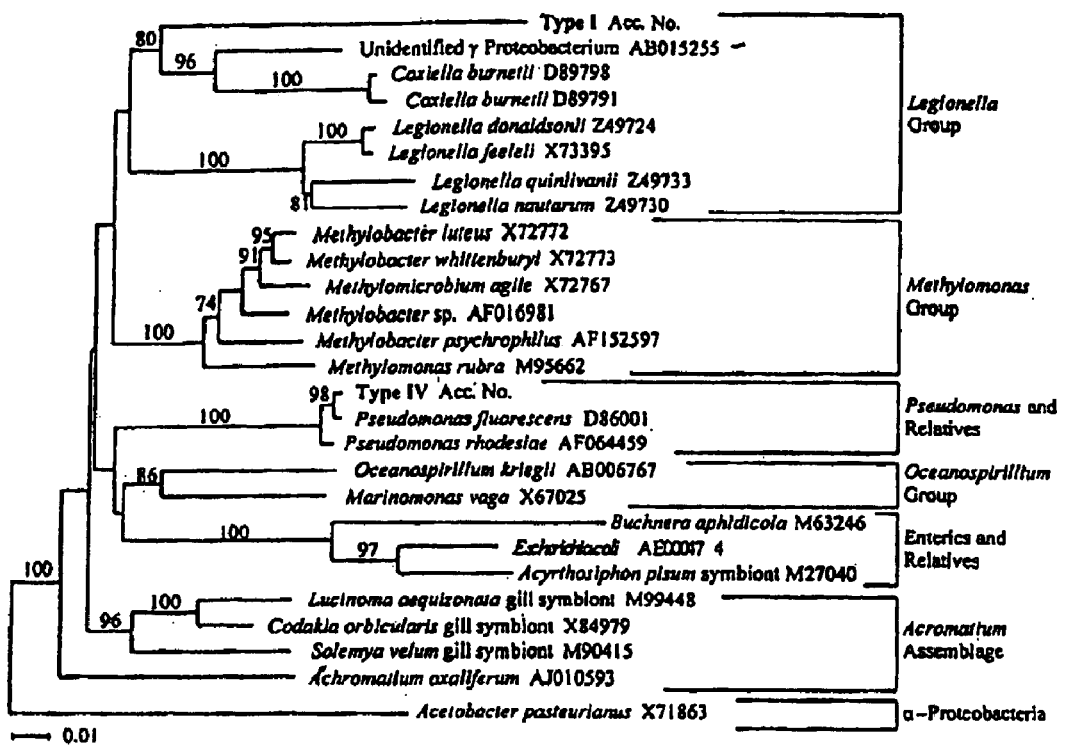

FIG. 2. Neighbour-joining analysis of 1288 bp from a total of 1451 bp of unambiguously aligned 16S rRNA gene sequences of Type-I (*Candidatus Endoecteinascidia frumentensis*) and IV with representative members of the gamma-Proteobacteria and an alpha-Proteobacteria outgroup. The values (>50%) at the nodes show the bootstrap support based on neighbour-joining analysis of 100 re-sampled data sets. The scale bar represents 0.01 substitutions per nucleotide position. Phylogenetic affiliations, based on RDP II assignments, are shown to the right of the tree. GenBank accession numbers are shown alongside each representative organism.

Figure 3:
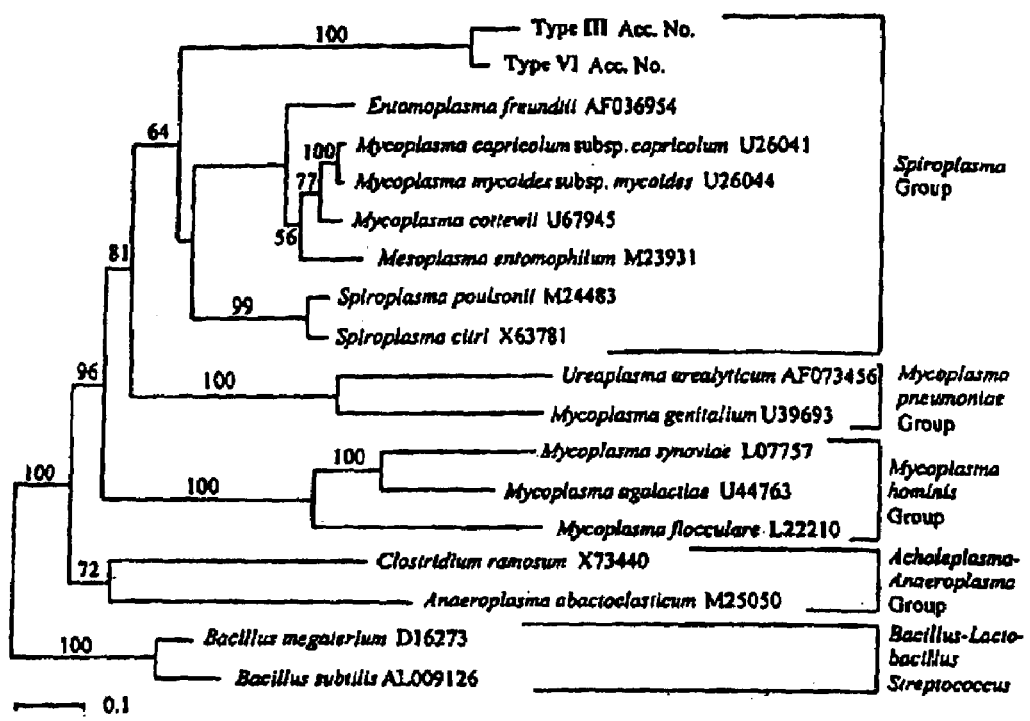

FIG. 3. Neighbour-joining analysis of 1289 bp from a total of 1417 bp of unambiguously aligned 16S rRNA gene sequences of Type-III and VI with representative members of the Gram positive low G+C % *Mycoplasma* and *Bacilli* as an outgroup. The values (>50%) at the nodes show the bootstrap support based on neighbour-joining analysis of 100 re-sampled data sets. The scale bar represents 0.1 substitutions per nucleotide position. Phylogenetic affiliations, based on RDP II assignments, are shown to the right of the tree. GenBank accession numbers are shown alongside each representative organism.

Figure 4:
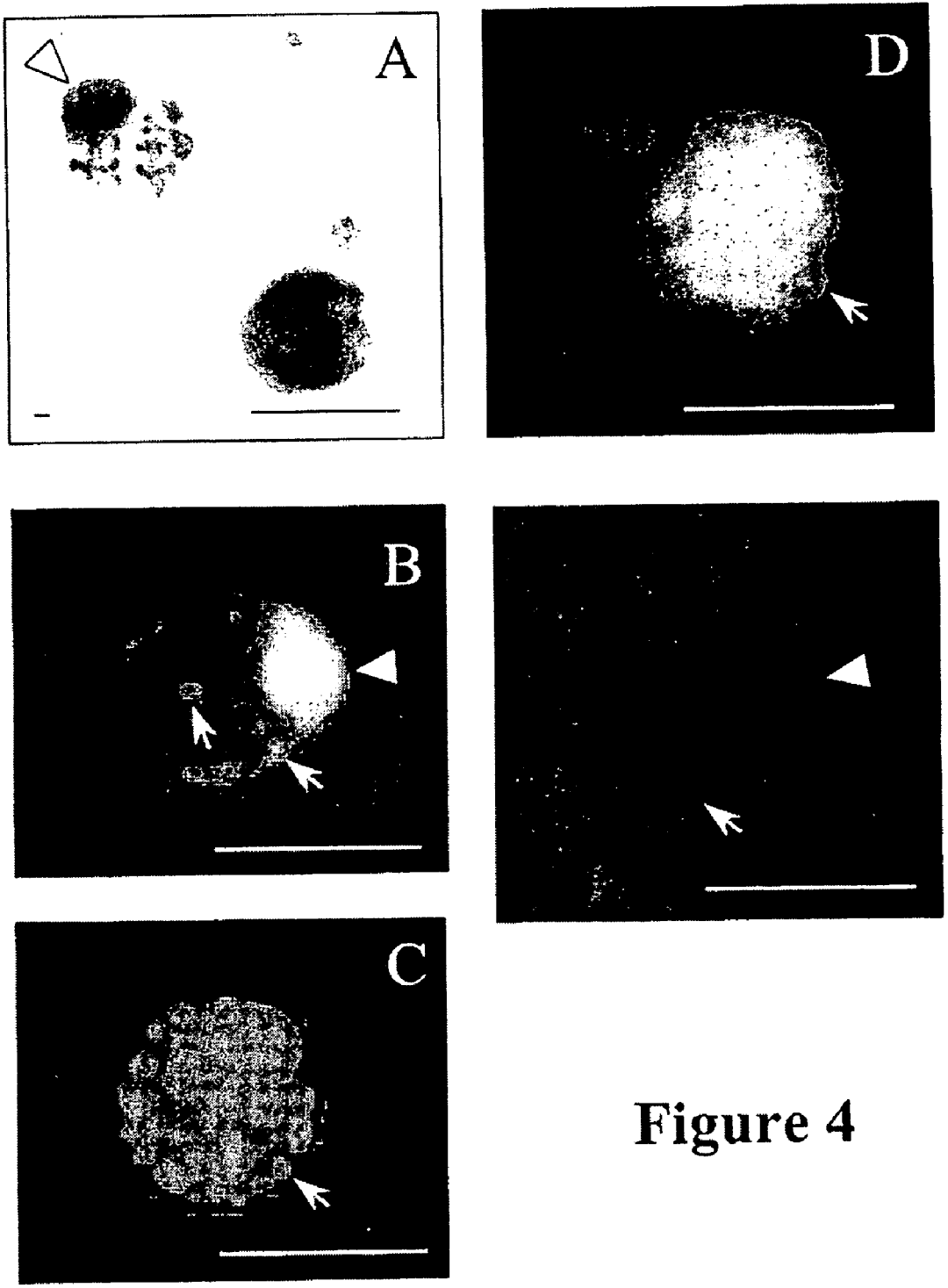

FIG. 4. Cytochemical and fluorescent staining of *E. turbinata* cells. Cells of dissociated buds were stained with several dyes (A: Hemacolor. B and C: Hoechst. D: Sytox) and fixed sections of adult zooids were stained with DAPI. Samples stained with fluorochromes were visualised under a fluorescent microscope. Fluorescent inclusions are visible with Hoechst, Sytox and DAPI (arrows). In some cases the cell nucleus also appears stained (arrowheads). Bars=10 μm.

Figure 5:

FIG. 5. Sections of *E. turbinata* larvae.

A: A section through a whole larva stained with haematoxylin and eosin. Major anatomical features are visible: s—siphons, t—tail, b—developing branchial basket, g—gut. Cells which hybridise with probe Eub338 are often located within the developing branchial area.

B to E: In situ hybridisation of larval tissue width the probe EUB338. Fluorescent cells indicate areas of probe binding (arrows).

B: A cluster of cells in the branchial basket with fluorescent inclusions.

C: Three cells from a similar area to (B).

D: Individual fluorescent inclusions are visible in this host cell.

E: Hybridised cells from a developing larva.

Bars (B–E)=10 μm. Bar (A)=250 μm

Figure 6:
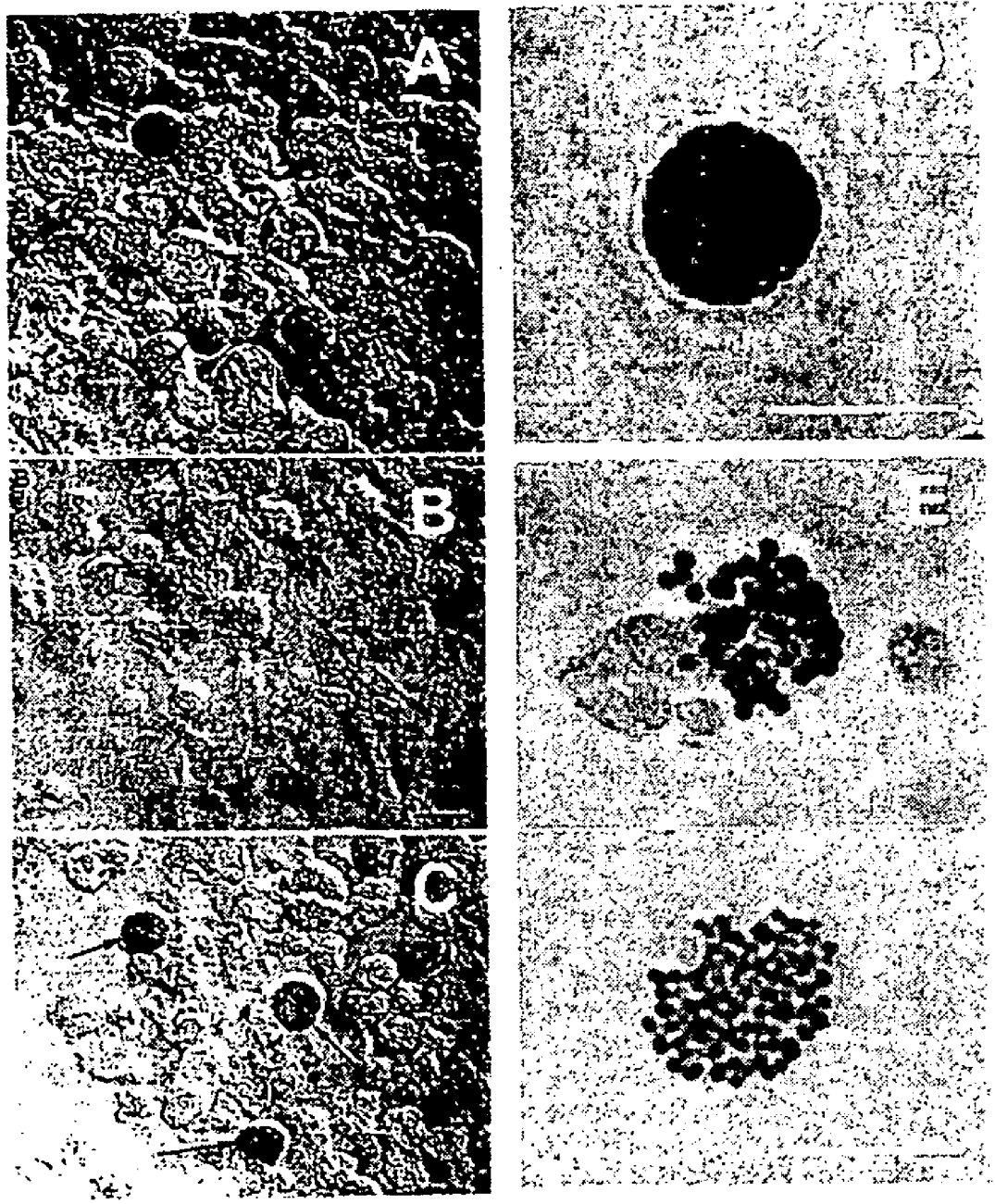

FIG. 6. In situ hybridisation of stolon tissue with the EUB338 probe, NonEUB338 probe and EFRU-F2 specific probe (A to C) and in situ hybridisation of dissociated bud cells with the EFRU-R1 probe (D-E), using alkaline phosphatase visualisation. A dark brown/black deposit shows area of probe binding.

A: Several cells show binding of the EUB338 probe (arrows).

B: The NonEUB338 probe shows a very low level of background binding.

C: The EFRU-F2 probe appears to be binding to a similar cell type (arrows).

D: Similar cells are positive on bud tissue with EFRU-R1 probe.

E: two cells showing the positive content as round-shaped elements.

Bars=10 μm.

Figure 7:

FIG. 7. Electron microscopy of larval tissue.

A: *E. turbinata* larval cell ('bacteriocyte') showing numerous putative bacterial inclusions (arrows). N=nucleus of host cell. Bar=2 μm.

B: High power image of these inclusions showing membrane detail.

Bar=1 μm

DETAILED DESCRIPTION OF THE INVENTION

The present inventors directed their efforts to analyse the bacterial flora associated with *Ecteinascidia turbinata*, and identify the most commonly occurring types both in larvae and adult tissues. These bacteria provide a potentially tractable (easily handled) model organism for examining this association as its secondary metabolites are well characterised and its larvae are known to be chemically defended. The presence of specifically associated bacteria, potentially an important factor in the chemical defense, provides an alternative source of ecteinascidin compounds.

Molecular methods were employed to ensure that all associated bacteria were represented, not just those which could be grown by conventional bacterial isolation and culture techniques. In situ hybridisation analysis using probes to 16S rRNA was carried out on larval, stolon, zooid and bud tissues of *E. turbinata* in an attempt to provide localisation information, in order to confirm the specificity of the associated bacteria and to identify potentially symbiotic strains.

Surprisingly we identified rDNA corresponding to an endosymbiotic bacteria, this bacteria appears to be responsible for the biosynthesis of ecteinascidin compounds.

The 16S rDNA sequence corresponding to *Candidatus Endoecteinascidia frumentensis* SEQ ID NO: 1 has been deposited in GeneBank with the accession number AY054370. The sequences derived from the other two strains associated with *E. turbinata* were deposited in GenBank, with the release of data withheld until the time of publication.

```
SEQ ID NO: 1
ATGAATTCTGGTGGCACTGCTTAACACATGCAAGTCGAACGGTAACATAA

TAAATGTTTTTTACATTTATGGATGACGAGTGGCGGACGGGTGAGTAACG

CGTAGGAACCTACCTTTTAGTGGGGGATAGCAGTGGGAAACTACTGGTAA

TACCGCATGATACTTTAGAGTTAAAACTAGCTGAATTTTATAGCTTGTGC

TAAAAGACGGGCCTGCGTTAGATTAGCTTGTTGGTAAGGTAACGGCTTAC

CAAGGCAACGATCTATAGCTGTTCTGAGAGGAAGATCAGCCACACTGGGA

CTGAGATACGGCCCAGACTCCTACGGGAGGCAGCAGTGGGGAATATTGGA

CAATGGGCGGAAGCCTGATCCAGCAATGCCACGTGTGTGAAGAAGGCCTT

CGGGTTGTAAAGCACTTTTATTAGCGAAGAAGATATAATGGTTAAGAGCT

TAATATATTTGACGTTAGCTAAAGAAAAAGCACCGGCTAACTCCGTGCCA

GCAGCCGCGGTAATACGGAGGGTGCAAGCGTTAATCGGAATTATTGGGCG

TAAAGAGCCTGTAGGTGGATAATTAAGTCAGATGTGAAATCCCAAAGCTT

AACTTTGGAACTGCATTTGAAACTAATTATCTAGAGTATAGTAGAGGGTA
```

```
-continued
GAGGAATTTCCGGTGTAGCGGTGAAATGCGTAGAGATCGGAAGGAACATC

AGTGGCGAAGGCGTCTACCTGGGACTAAAACTGACACTGAGAGGCGAAAG

CATGGGGAGCAAACAGGATTAGATACCCTGGTAGTCCATGCCGTAAACTA

TGAGTACTAACTGTTGGAATTTTTAAATTTTAGTAGTGGAGCTAACGCAA

TAAGTACTCCGCCTGGGGATTACGGCCGCAAGGCTAAAACTCAAAGGAAT

TGACGGGGGCCCGCACAAGCGGTGGAGCATGTGGTTTAATTCGATGCAAC

GCGAAAAACCTTACCTACTCTTGAAATCCTTCGTACTTTATAGAGATATA

AAGGTGCCTTTGGAACGAAGTGACAGGTGCTGCATGGCTGTCGTCAGCTC

GTGTCGTGAGATGTTGGGTTAAGTCCCGTAACGAGCGCAACCCTTTCCCT

TAGTTGCCAGCGTGTAAAGACGGGGACTCTGAGGGGACTGCCGGTGATAA

ACCGGAGGAAGGCGAGGACGACGTCAAGTCATCATGGTCCTTACGAGTAG

GGCTACACACGTGCTACAATGGTATGTACAAAGGGAGGCAAAATTGTAAA

ATCTAGCAAATCCCCAAAAGCATATCTTAGTCCGGATTGAAGTCTGCAAC

TCGACTTCATGAAGTTGGAATCGCTAGTAATCGCGAATCGCATGTCGCGG

TGAATACGTTCCCGGGCCTTGTACACACCGCCCGTCACACCACGGAAGTG

GAATGCACCAGAAGTGGCTAGGATAACCGAAAGGAGTCCGGTCCCTACGG

TGTGTTTCGTAACTGGGGTGAAGTCGTAACAAGGTAGCCGTAGGGAACTG

C
```

The present invention provides one of the first reports of endosymbiotic bacteria in an ascidian. The combination of 16S rRNA gene analysis, in situ hybridisation and electron microscopy, provides evidence for a specific association between these bacteria and the ascidian host cells. The observation of identical bacteria strains, with similar levels of dominance, and of similar cell types, in both adult (zooid and stolon) and larval tissues provide strong indications that these cells are a consistent and important feature of *Ecteinascidia turbinata*. In situ hybridisation based on the obtained sequence data suggest that the *Candidatus Endoecteinascidia frumentensis* (Type I strain) is the observed symbiont. Besides that, we found the presence of this bacterial strain in all the development stages and in samples collected all over the world, and the absence of it in a related tunicate from the same geographic area.

16S rDNA sequence analysis of dominant bacterial strains in *E. turbinata* has identified three novel strains. *Candidatus Endoecteinascidia frumentensis* falls in the gamma-proteobacteria subdivsion. Although it is only distantly affiliated to any other known strains within this group, it bears similarities to species in the *Legionella* and *Oceanospirillum* subgroups. Many previously described marine endosymbionts belong to the gamma-proteobacteria subdivision, with representatives from sponges, oligochaetes and bryozoans covering a range of ecological niches and putative activities.

The spiroplasm-like Type III and VI-symbionts appear to represent a new sub group. Mycoplasms are often found as parasitic organisms in vertebrates and invertebrates, although there is increasing evidence to support both commensal and saprophytic roles. There are few records of them in marine invertebrates, although they have been identified in a bryozoan. The significance of finding a Gram negative bacteria (the gamma-proteobacterium), together with two common Gram positive strains (the spiroplasms), in *E. turbinata* is not known, but it is interesting to note that a similar situation occurs in aphids. Localisation of the mycoplasmas in *E. turbinata* would be a valuable step forward.

The use of molecular techniques to survey bacterial populations has allowed comprehensive analysis of bacterial complement, overcoming selection for bacteria that are culturable by standard methods. Use of 16S rRNA gene sequences to identify bacteria is now the standard procedure for analysis of bacteria in environmental samples and has enabled much of the current progress in the area of bacterial symbiosis. Whilst being suitable for surveying of bacterial strains, this technique can lead to misinterpretation if attempting to quantify those types present and analysis of results must take note of these possible failings. For example, it has been found that templates containing GC-rich combinations in the priming sites, might be preferentially amplified.

However, the results presented below indicate such a high predominance of one novel strain, in four different tissues, that it is unlikely this could be explained by PCR bias. Similarly, bacterial types possess a different number of copies of the 16S rRNA gene, leading to potential weighting of amplification results. For example, the spiroplasm-like strains identified are likely to possess only one copy of the gene, whereas the gamma-proteobacteria strain may contain two or more. In the case of *E. turbinata* the clear predominance of strains in all tissues examined and in all the locations tested, negate the possibilities of interpretation errors.

Cytochemical studies and in situ hybridisation using the universal probes described in the examples suggests that bacteria are located within host cells in adult and larval tissue. It appears that these cells are free, possibly in the blood, and present at higher densities in the larvae. Here, they are clustered primarily in the developing branchial basket This high density of bacteria supports the dominance observed in the 16S analysis of larval tissue, and together with in situ hybridisation using the probe to the *Candidatus Endoecteinascidia frumentensis* sequence, adds weight to the evidence that this strain is the one identified in situ.

The significance of the high numbers of 'bacteriocytes' in the branchial basket is not clear, as the larvae are not feeding, but it suggests that the bacteria may be present at sites of optimal nutrition (gaseous and nutrient exchange) as soon as the larvae has settled and the siphons have opened. However, it is also possible that a high density in this area is a side effect of the developing branchial system and that the bacteriocytes are clustered here due to blind ending blood vessels that are still growing to form the basket. Higher densities of putative bacteriocytes are also found in the stolon, which becomes engorged with cells as colonies regress. Few cell types are present, suggesting that cells have become undifferentiated, or are primarily for storage, ready to support the next phase of budding. Buds also show high density of bacteriocytes, which have probably migrated from the stolon directly. However, labeled cells are much harder to detect in zooids, where tissue is diffuse and cell density low. Still several putative bacteriocytes have been observed by in situ hybridisation, with similar characteristics as before. That is, not anchored, but freely circulating, possibly in the blood.

The forming branchial basket was the target tissue for TEM studies based on the in situ hybridisation results. The presence of bacteriocytes of similar size and apparent morphology as the cells illuminated by hybridisation in the branchial basket and in dissociated bud cells suggests that the TEM results are the same cells as those seen by hybridisation. The bacteria appear to be intracellular symbionts rather than pathogens or ingested bacteria. This is suggested from a number of observations: i) there is no obvious endocytotic behaviour by the cells; ii) the bacteria appear healthy; iii) there is no obvious pathology of the host cell in the smaller bacteriocytes; iv) the presence of so many polyribosomes suggests a large amount of synthetic activity by the cell that is intended for internal consumption rather than export; v) the bacteria appear to be of a uniform type and the same type has been observed in different individual larvae. A double membrane appears to surround the bacteria, suggesting that they are gram negative. However, the method of fixation was not optimal and further investigations of the fine structure of the bacteriocytes may help to confirm this observation.

The presence of the bacteria in non-feeding larvae strongly suggests that they are vertically transmitted through the eggs and larvae at egg formation or during brooding. This transmission mechanism is also observed in other marine species, for example in the ascidian *Diplosoma similes*, and in some bivalves. Intraovarial transmission of symbionts is also common in insects. That the bacteria are endocytotic and likely to be vertically transmitted also suggests that they are unlikely to be culturable in simple media. Culturing experiments followed by 16S RFLP analysis of 22 bacterial strains derived from larvae, and 9 from zooids, indicate that bacteria similar to the Type I, III and VI strain did not grow under standard conditions. The difficulty in culturing symbiotic bacteria is a barrier to the further elucidation of their roles and methods to overcome this problem are needed. Some researchers have managed to grow a symbiont of *Theonella* using specific culture conditions. Efforts to culture intracellular symbionts have been limited and attempts to culture host cells have generally failed. Ways of re-addressing this problem would greatly improve the understanding of bacterial symbioses in general.

The symbionts of *Ecteinascidia turbinata* appear to be involved in the biosynthesis of ecteinascidins. Many marine symbionts are thioautotrophs from anoxic environments, oxidising sulphur and fixing $CO_2$. Indeed a complete sulphur cycle involving two symbionts has recently been elegantly demonstrated in a marine oligochaete. In the case of *E turbinata* it is possible that utilisation of certain nutrients in a potentially anoxic mangrove environment may be advantageous, although *E. turbinata* is known to grow and thrive in a range of habitats.

*E turbinata* larvae and adults are vulnerable to predation and/or fouling, thus production of noxious compounds may act as an effective defensive strategy. That the larvae are chemically defended, known to contain secondary metabolites and also house a large population of apparently endosymbiotic bacteria may be circumstantial. However, it is possible that a symbiosis between the ascidian and a secondary metabolite-producing bacterium may confer this chemical protection.

Therefore, the rDNA sequence of the present invention can be used in an assay to indentify the symbiont and to isolate its DNA, for example with the widely used walking chromosome techniques. This DNA can be responsible for the biosynthesis of the ecteinascidin compounds of at least of bioprecursors or intermediates thereof. Once isolated it can be introduced in a host cell to provide a microorganism producing ecteinascidin compounds, providing an alternative source of these valuable compounds.

Accordingly, the invention provides a process for producing an ecteinascidin compound, precursor or intermediate thereof, or a compound involved in biosynthesis of an ecteinascidin compound, precursor or intermediate, comprising culturing such a host cell under conditions sufficient for biosynthesis of said ecteinascidin compound, precursor or intermediate thereof, or said compound involved in biosynthesis of an ecteinascidin compound, precursor or intermediate.

The process can further comprise recovering the ecteinascidin compound, precursor or intermediate thereof, or compound involved in biosynthesis of an ecteinascidin compound, precursor or intermediate thereof from the culture.

EXAMPLES

Tissue Preparation and Dissection:

*Ecteinascidia turbinata* colonies were obtained from the Mediterranean Sea (Formentera, Spain) and Atlantic Ocean (Cádiz, Spain) and transferred to a marine aquarium at a water temperature of 24° C. Larvae were obtained from ripe colonies which were undergoing larval release, or by dissection from these colonies. They were rinsed several times in sterile filtered seawater before DNA extraction. Immature zooids (without gonads or larvae) were pinched off the colony at the stolon and incubated in sterile seawater at 24° C. for 24 hours, with one change of water. They were then given a final rinse in sterile seawater and prepared for DNA extraction. Stolons from regressing colonies were removed and rinsed in sterile seawater. They were gently homogenised to liberate cells and this supernatant was removed to another tube, discarding the larger debris. The cells were spun down and pelleted, ready for DNA extraction. All material was snap frozen in liquid nitrogen for storage at −80° C. Scallop muscle (*Chlamys opercuilars*) was removed from an animal held in the aquarium, rinsed in sterile seawater and used as a control.

Example 1

16S rDNA Analysis and RFLPs

DNA Isolation, 16S rDNA PCR Amplification and Cloning:

All DNA manipulations were performed under recognised standard conditions. To ensure all cells, both eukaryotic and prokaryotic, were broken open, the tissue was homogenised in liquid nitrogen in a sterile mortar and pestle (except the stolon cells which were used directly). DNA was isolated either using a GNOME DNA Isolation kit (BIO101, Vista, Calif.), or with the following protocol. Lysis buffer (100 mM Tris-HCI, 10 mM EDTA, 150 mM NaCl, 100 µg/ml RNase A) was added to the frozen powder and allowed to thaw. The homogenised tissue was transferred to a sterile 1.5 ml centrifuge tube, lysozyme was added (200 pg/ml final concentration) and the sample incubated for 10 minutes at 37° C. Proteinase K and SDS were added (400 pg/ml and 1% final concentrations, respectively) and the suspension incubated for a further 30 minutes at 37° C. DNA was purified by two sequential extractions with Tris-HCI (pH 8.0) equilibrated Phenol:Chloroform:Isoamyl alcohol (25:24:1), twice with Chloroform:Isoamyl alcohol (24:1), ethanol precipitated with sodium acetate (pH 5.2) and washed with 70% ethanol. The DNA pellet was air-dried and stored in TE buffer (10 mM Tris-HCI, pH 8.0; 1 mM EDTA) at −20° C.

Two different universal 16S rDNA bacterial PCR set of primers and one set of specific oligonucleotides for DNA sequences of the *Candidatus* Endoecteinascidia frumentensis 16S rDNA were used for the amplification experiments. The universal primers were: forward, 8-AG(AG) GTT TGA TC (AC) TGG CTC AG-27 (SEQ ID: 9); reverse 1509-G (GT)T ACC TTG TTA CGA CTT-1494 (SEQ ID: 10) (primer position is according to *E. coli,* Weisburg, W. G., Barns, S. M., Pelletier, D. A. & Lane, D. J. 1999. 16S ribosomal DNA amplification for phylogenetic study. J. Bac. 173, 607-703.) and 16SF1 5'-GAG A(G/C)T TTG ATC (A/C/T)TG GCT CAG-3' (SEQ ID:11); 1600R 5'-AAG GAG GTG ATC CAG CC-3' (SEQ ID: 12) (modified from Dorsch, M. & Stackebrandt, E. 1992. Some modifications in the procedure of direct sequencing of PCR amplified 16S rDNA. J. Microbiol. Methods, 16, 271-279), and the specific ones were EFRU-F1, 5'-CGG TAA CAT AAT AAA TGT TTT TTA CAT TTA TG-3' (SEQ ID:2) and EFRU-R1, 5'-TAT GCT TTT GGG GAT TTG CTA GAT T-3' (SEQ ID:3) (this study). A DNA Engine (MJ Instruments, USA) thermocycler, or a Mastercycler personal (Eppendorf, Germany) was used, cycled as follows: 94° C. for 2 min., followed by 30 cycles of 55° C. (30secs), 72° C. (1 min 15s) and 94° C. (15s), and a final elongation step of 72° C. for 10 minutes. Total bacterial 16S rDNA from the extracted DNA was amplified from several dilutions to obtain optimal results and a "no-DNA" control was run for each PCR mix. The PCR product was confirmed by 1% agarose gel electrophoresis and ethidium bromide staining.

When needed, the PCR products were purified (Millipore Ultrafree-DA columns) and ligated into pGEM-T (Promega, USA) overnight at 4° C. to 16° C. and then transformed into competent *E. coli* DH5α (Life Technologies, UK). Transformants were spread on LB agar containing 50 pg/ml ampicillin, 0.2 mM X-gal and 0.16 mM IPTG for blue-white screening, and incubated overnight at 37° C.

RFLP Analysis of Selected Clones and Sequencing:

Putative insert-containing clones (100 clones from each of the larval, zooid and stolon, and 40 from the scallop-control material) were selected from the *E. coli* plates by picking with a sterile toothpick and emulsifying into a 50 pl PCR reaction containing M13/pUC universal primers (forward 5'-GTT TTC CCA GTC ACG AC-3' (SEQ ID:13); reverse 5'-CAG GAA ACA GCT ATG AC-3' (SEQ ID:14)) and patched onto LB agar containing ampicillin, X-gal and IPTG (as above) for subsequent plasmid isolation. PCR reactions were cycled as follows: 94° C. for 5 minutes, followed by 30 cycles of 50° C. (30 secs), 72° C. (1 min 30 s), 94° C. (15 secs), with a final elongation step of 72° C. for 10 minutes. Inserts of the appropriate size (approximately 1700 base pairs) were confirmed by 1% agarose gel electrophoresis. Positive PCR products were ethanol precipitated and resuspended in sterile distilled H$_2$O. Restriction fragment length polymorphism (RFLP) analysis was carried out using the restriction enzymes HaeIII and HhaI (Promega, USA). The restricted PCR products were electrophoresed through a 1x Tris- acetate (40 mM), EDTA (1 mM), 3% wide-range agarose gel (Sigma, USA) and stained with ethidium bromide. Kodak 1-D system and software (Kodak, USA) was used to capture the resultant RFLP patterns. Clones representative of each different pattern observed were isolated and grown up in LB broth with ampicillin (75 pg/ml) overnight and stored frozen with 10% glycerol at −80° C. Plasmid DNA was isolated from representative clones for DNA sequence analysis according to the manufacturers instructions (Qiagen Spin Mini-Preps, UK). DNA sequencing was performed using the M13 universal primers and ABI BigDye chemistry (PE Applied Biosystems, USA) and analysed on an ABI 377 DNA sequencer (PE Applied Biosystems, USA).

Results:

The first approach to the analysis of the microorganisms associated to *Ecteinascidia turbinata* was done using total DNA isolated from adult zooids. Direct sequencing of the PCR amplification fragment obtained with this DNA and "universal" eubacterial primers 16SF 1 (5'-GAGA(G/C) TTTGATC(A/C/T)TGGCTCAG-3' (SEQ ID:11)) and 1600R (5'-AAGGAGGTGATCCAGCC-3' (SEQ ID:12)) (modified from Dorsch & Stackebrandt, 1992) resulted in a clean sequence, indicating the prevalence of this microorganism in the tunicate. It is defined above as SEQ ID 1.

With the aim to confirm this result, specific oligonucleotides were designed for the *Candidatus Endoecteinascidia frumentensis* 16S rDNA. These oligonucleotides (EFRU-F1, 5'-CGG TAA CAT AAT A AA TGT TTT TTA CAT TTA TG-3' (SEQ ID:2) and EFRU-R1, 5'-TAT GCT TTT GGG GAT TTG CTA GAT T-3' (SEQ LD:3)) were used as primers for the PCR amplification experiments performed with total DNA isolated from adult zooids from different locations around the world (Formentera, Menorca, Túnez, Cádiz, Cuba, Florida, Puerto Rico) and with DNA obtained at different phases of development (stolon, embryos, larvae, buds and adult zooids). An amplification band with the expected size was obtained in all the cases, and RFLP and sequence analysis showed that *Candidatus Endoecteinascidia frumentensis* was present in all those samples. As a control, total DNA from a closely related organism, *Ecteinascidia conklini* was isolated, and PCR experiments were performed. No amplification was obtained with the *Candidatus Endoecteinascidia frumentensis* specific primers, although bands of the right size could be seen when universal eubacterial primers were used (data not shown). Positive results were also obtained when *E. turbinata* DNA was used (both with a sample collected at the same area as *E. conklini* was and with a sample from a different location), with universal and specific primers.

The major presence of *Candidatus Endoecteinaseidia frumentensis* was confirmed by the analysis of the bacterial flora associated with the tunicate. To minimise the contribution of non-specifically associated bacteria contaminating the total DNA pool, tissue was cleaned as far as possible before DNA extraction. The incubation of live animals is sterile seawater helped to depurate (cleanse) the pharynx and gut of *E. turbinata,* which would have contained large numbers of non-specifically associated bacteria. Near full-length 16S rRNA gene fragments were amplified from the total DNA extracted from zooid, larval, stolon tissue and the control, scallop abductor muscle. After cloning and RFLP analysis, percentage dominance was assigned to the patterns observed in the three tissue types in order to determine any commonly occurring types. Four types were identified as occurring in all three tissue types and which also represented the most abundant RFLP types (see Table 1 and FIG. 1). The Type I pattern was the most common, representing between 42-67% of RFLP patterns observed in the three tissue types and the sequence analysis of this Type showed that it actually was *Candidatus Endoecteinascidia frumentensis.* Types VI, III and IV were the remaining three most abundant patterns Table 1, FIG. 1). The scallop control data showed no Type I (*Candidatus Endoecteinascidia frumentensis*), III or VI patterns, but a Type IV pattern was observed. This, together with the sequence analysis, identified Type IV as a commonly occurring marine-associated bacteria, and unlikely to have a specific relationship with *E turbinata*.

TABLE 1

Dominance of RFLP patterns from zooid, larval and stolon material, and the total number of patterns observed.

| RFLP Type (Pattern) | % dominance of RFLP types in *E. turbinata* tissue | | |
|---|---|---|---|
| | ZOOID | LARVAE | STOLON |
| Type I (*Candidatus Endoecteinascidia frumentensis*) | 42.6 | 55.9 | 67.0 |
| Type III | 5.6 | 9.6 | 5.3 |
| Type IV | 7.8 | 1.0 | 4.2 |
| Type VI | 14.6 | 4.3 | 10.0 |
| Total number of clones digested | 89 | 93 | 94 |
| Total number of patterns observed | 21 | 11 | is |

Example 2

Phylogenetic Analysis

Compiled DNA sequences from two or more independent clones of each RFLP type sequenced were aligned with the RDP II database (Maidak B L, Cole J R, Lilburn T G, Parker C T Jr, Saxman P R, Farris R J, Garrity G M, Ohsen G J, Schmidt T M, Tiedje, J M. 2001. The RDP-II (Ribosomal Database Project). Nucleic Acids Res. 29, 173-174) using SEQUENCE MATCH and checked with CHIMERA CHECK to ensure that no sequence was chimeric. Phylogenetic inference of the novel 16S rDNA sequences was achieved by aligning the compiled 16S rDNA sequences with representative sequences obtained from the RDP II (Madiak et al., 2001) and GenBank using CLUSTALX (Thompson, J. D., Gibson, T. J., Plewniak, F., Jeanmougin, F. & Higgins, D. G. (1997). The ClustalX windows interface: flexible strategies for multiple sequence alignment aided by quality analysis tools. Nucleic Acids Research 24, 4876-4882.). Alignments were manually corrected and ambiguous positions removed. PAUP* 4.0b8 (Swofford, D. L. (2001). PAUP*. Phylogenetic Analysis Using Parsimony (*and Other Methods). Version 4. Sinauer Associates, Sunderland, Mass.) was used to infer phylogenetic trees using parsimony and neighbour-joining analysis according to the Kimura 2-parameter model of nucleotide substitution (Kimura, M. (1980). A simple method for estimating evolutionary rate of base subsitutions through comparative studies of nucleotide sequences. J. Mol. Evol. 16, 111-120) and assuming the among-site rate variation having a gamma distribution shape of 0.5. Bootstrap support for the inferred tree was established following re-sampling of 100 data sets based on neighbour-joining analysis.

Results:

Four near complete 16S rRNA genes of the most commonly occurring bacterial strains were sequenced. Alignment of these sequences with the RDP II database indicated that the 16S rRNA gene sequences of Types I (*Candidatus Endoecteinascidia frumentensis*), III and VI were unrelated to any particular bacterial species in the database. The Type IV pattern was shown to have 98% sequence similarity with *Pseudomonas fluorescens* (D86001). Type I (*Candidatus Endoecteinascidia frumentensis*) could be reliably assigned as a member of the Gram negative, gamma-Proteobacteria (FIG. 2). Within this group, it showed a closer relationship to the *Legionella* group. However, the deep divergence and long branch-length of this sequence makes this a tentative assignment. This was reinforced by parsimony analysis, which was not able to conclusively support the branching order as depicted in FIG. 2. The closest sequence affiliation to *Candidatus Endoecteinascidia frumentensis* was an unidentified gamma-Proteobacteria (AB015255) isolated from the sediment of a deep-sea trench. Types III and VI shared 97.3% sequence similarity to each other. Phylogenetically, they were most similar to *Spiroplasma* group, which are members of the low G+C % Gram positive *Mycoplasma* and relatives (FIG. 3). Both Type III and VI, although deeply divergent from within the *Spiroplasma* group, could be reliably assigned to this group of the *Mycoplasmas*.

Example 3

Cytochemical and Fluorescent Staining

Dissociation of Buds:

*Esteinascidia turbinata* stolon was obtained from Cádiz (Spain) and transferred to a marine aquarium at a water temperature of 24° C. New generations of growing buds were collected from the stolon and washed several times in sterile filtered seawater. Bud tunic was removed using forceps under sterile conditions and nude buds (20-30) were washed four times in sterile seawater. Buds were placed in dissociation medium (sterile seawater plus 0.1% collagenase), and incubated for 3 hours at 27° C. Bud tissue was dissociated by pipetting. To obtain a suspension of single cells, sample was left to decant on the bench for 3 minutes. The upper part of the sample was saved to other tube and cells concentrated by centrifugation at 1200 rpm/RT/4 minutes. Cells were washed with 500 µl of sterile seawater, centrifuged again and resuspended in 100 µl of fixation media.

Cell Fixation and Slide Preparation for In Situ Hybridisation of Single Cells:

*E. turbinata* single cells were fixed at RT for 30 minutes in 100 µl of fixation media (4% formaldehyde, 5% acetic acid in sterile seawater). Fixed cells were washed with 500 µl of sterile seawater, resuspended in 20 µl of sterile seawater and spread on a glass slide. Slides were previously treated with TESPA in order to improve cell attachment. Slides were air dried, washed with sterile seawater and stored in 70% ethanol (5° C.) until performing in situ hybridisation.

Cell Staining

Samples of dissociated and fixated bud cells were stained with Hoechst-33342, Dapi, Sytox or Hemacolor, for 15 minutes. Cells were centrifuged (1200 rpm/RT/4 minutes), resuspended in 250 µl of sterile seawater and observed under UV light in a inverted fluorescent microscope (Leica DM IRB).

Results:

Dissociated bud cells or fixed sections of adults were used for several staining experiments in order to identify intracellular microorganisms in *E. turbinata* cells. By using Hemacolor, a general staining method, intracellular positive granules could be observed in some cells of dissociated buds (FIG. 4A). Several fluorescent dyes specific for nucleic acids were also employed. These dyes are sensitive enough to allow detection of DNA/RNA containing particles as bacteria and mycoplasms, but not subcellular organelles as mitochondria or chloroplasts. Hoechst and Sytox showed intracellular positive elements in cells of dissociated buds. In some cases, just a few fluorescent round or rod-shaped elements were observed inside large vacuoles (FIG. 4B) but also dense stained cells showing a granular appearance could be detected (FIGS. 4C and D). In fixed sections of E. turbinata zooids, DAPI staining showed the same type of fully stained cells (FIG. 4E). The cell nucleus is visible in some cases (FIGS. 4A, B and E), when not hidden by fluorescent particles (FIGS. 4C and D).

Example 4

In Situ Hibridisation with a Universal Probe

In situ hybridisation was carried out using standard methods. Tissue was fixed in 4% Paraformaldehyde (PFA) in TBS (0.1MTris-HCI, 0.9% NaCl) with 0.1M MOPS at room temperature for 30 mins to 1 hour. It was then embedded in paraffin wax, sectioned, and sections were mounted on gelatin-coated slides. Two panels of sections were mounted on each slide, placing alternate sections on each panel, to provide a test and control panel of the same area of the tissue. The slides were then prepared for hybridisation. In brief, after rehydration they were rinsed, incubated in 1 μg/ml Proteinase K, post-fixed in 4% PFA in TBS for 10 minutes, rinsed and treated with 0.25% acetic anhydride in 0.1M Triethanolamine-HCI pH8, dehydrated and air dried, ready for storage at –80° C.

Initial in situ hybridisation studies were carried out using a biotinylated universal bacterial 16S rRNA probe to identify sites of potential interest (EUB338 5'-GCT GCC TCC CGT AGG AGT-3' (SEQ ID:7), and a control probe NON-EUB338 5'-ACT CCT ACG GGA GGC AGC-3' (SEQ ID:8)) (Amann, R. I. Binder, B. J., Olson, R. J., Chisholm, S. W., Devereux, R. & Stahl, D. A. 1990. Combination of 16S rRNA-targeted oligonucleotide probes with flow cytometry for analysing mixed microbial populations. Appl. Environ. Microbiol. 56, 1919-1925.). Other controls consisted of incubations with no probe, and panels of attached bacterial cells (E. coli) which had been fixed and processed as the sections. Hybridisation was carried out at 45° C. for 3 hours in buffer (0.9 M NaCl, 20 mM Tris-HCl pH7.2, 1× Denhardts, 0.1% SDS, 5 mM EDTA, 0.1 mg/ml Poly (A)) with 2.5 ng/μL of probe which had been reconstituted in TE. Hybridisation chambers with dual ports were used to prevent evaporation (Grace BioLabs: 22 mm×22 mm chamber for each panel of sections on the slide). Following hybridisation the slides were washed 2×15 minutes in wash buffer (0.9 M NaCl, 20 mM Tris-HCl pH 7.2, 0.1% SDS) at 48° C. Binding of probe was visualised using Avidin-DN (Vector Labs) as recommended by the manufacturer. Sections were mounted in Vectorshield (Vector Labs) and viewed on a Zeiss Axioskop with fluorescent attachments. For visualisation with alkaline phosphatase (AP) the slides were washed after hybridisation and incubated in AP conjugated anti-biotin antibody (Vector Labs) diluted 1:1000 in buffer (20 mM sodium phosphate, 0.9% Tween, 0.1% BSA) at 4° C. overnight. They were then washed and visualised using a BCIP/NBT-AP substrate kit (Vector Labs).

Results:

Hybridisation of the universal bacterial EUB 338 16S rRNA probe was observed in larval sections (FIG. 5), stolon material and at low levels in zooid sections. Positive in situ hybridisation was found in cells of approximately 10-12 μm diameter which demonstrate a granular appearance. These cells usually had an unstained area at one pole, which was thought to be the host cell nucleus. In larvae the cells were predominantly found in the developing branchial basket (FIG. 5). In zooid tissue, only a few positively hybridising cells were observed. These cells were located in the region of the pharynx and with cells possibly associated with blood vessels. The background fluorescence was relatively high, but hybridisation positive cells were easily distinguishable on the test sections, but were clearly not present in the controls. Dissected portions of regressing stolon and budding tissue were also examined by fluorescent in situ hybridisation. With these preparations, the background fluorescence under the FITC filter was too high to facilitate accurate interpretation of hybridisation. Consequently, subsequent hybridisation experiments used the histochemical AP visualisation system. Hybridising cells were found scattered throughout the stolon and bud tissue. The appearance of the hybridisation-positive cells in the stolon and bud tissue had the same general appearance as observed in the larvae, with the hybridised part of the cell exhibiting granular staining and an unstained, approximately polar region, presumably representing the host nucleus (FIG. 6A). The non-Eub338 probe gave very low levels of background binding using the AP system, such that it was almost indiscernible when compared to the intensity of Eub338 binding (FIG. 6B). In all cases where the control was buffer without probe, the cells hybridised in the test sections could not be observed in the control sections.

Example 5

Specific Probes: Dot Blots and In Situ Hybridisation

Probes were designed to putatively unique regions of the Candidatus Endoecteinascidia frumentensis and Type III 16S rDNA sequences:

TABLE 2

| Oligonucleotide | Sequences (5'-3') | Application[a] | References |
|---|---|---|---|
| Symbiont specific | | | |
| EFRU-F1 | CGG TAA CAT AAT AAA TGT TTT TTA CAT TTA TG | P, I, S | Herein |
| EFRU-R1 | TAT GCT TTT GGG GAT TTG CTA GAT T | I, D, S | Herein |
| EFRU-R2 | CTT TCG GTT ATC CTA GCC AC | I, D | Herein |

TABLE 2-continued

| Oligonucleotide | Sequences (5'-3') | Application[a] | References |
|---|---|---|---|
| Domain bacteria | | | |
| Type III-1 | GCA ACT ATT TCT AGC TGT TAT TC | D | Herein |
| Type III-4 | AGC TTT GCA CTG GAT GTC AAG | D | Herein |
| EUB338 | GCT GCC TCC CGT AGG AGT | I, D | Amann et al., 1990 |
| NON-EUB338 | ACT CCT ACG GGA GGC AGC | I | Amann et al., 1990 |
| EUB8-f | AG(AG) GTT TGA TC(AC) TGG CTC AG | P, S | Weiburg et al., 1999 |
| EUB1509-r | G(GT)T ACC TTG TTA CGA CTT | P, S | Weiburg et al, 1999 |
| 16S-F1 | GAG A(G/C)T TTG ATC (A/C/T)TG GCT CAG | P, S | Modified from Dorsch & Stackebrandt, 1992 |
| 1600R | AAG GAG GTG ATC CAG CC | P, S | Modified from Dorsch & Stackebrandt, 1992 |
| Universal primers | | | |
| M13/pUC-f | GTT TTC CCA GTC ACG AC | S | |
| M13/pUC-r | CAG GAA ACA GCT ATG AC | S | |

[a]P = PCR primer; I = In situ hybridization probe; D = Dot-blot probe; S = Sequencing primers Probe specificity was initially examined by submitting the probe sequence to the SEQUENCE MATCH and PROBE MATCH on the RDP II database (Maidak et al., 2001) and compared to *E. coli* 16S secondary structure to check for optimal regions of binding (Amann, R. I., Ludwig, W. & Schleifer, K-H. 1995. Phylogenetic identification and in situ detection of individual microbial cells without cultivation. Microbiological Reviews. 59, 143-169; Zheng, D., Alm, E. W., Stahl, D. A. & Raskin, L. 1996. Characterisation of universal small-subunit rRNA hybridisation probes for quantitative molecular microbial ecology studies. Appl. Environ. Microbiol. 62, 4504-4513).

Conditions for probe binding were confirmed by dot blot analysis. 16S rDNA PCR products from the Type I *Candidatus Endoecteinascidia frumentensis*, III, IV & VI plasmid clones (50 ng) and *E. coli* DH5 alpha were spotted onto a positively charged nylon membrane as per manufacturers instructions (Schleicher & Schuell). The membranes were prehybridised at 46° C. for 1 hour in hybridisation buffer (as previously plus 2% Marvel), and then hybridised at 46° C. for 3 hours with 0.5 ng/µl of probe. Membranes were washed 2×15 minutes at 50° C. (wash buffer as before), blocked in NaPBS (20 mM sodium phosphate, 0.9% NaCl) with 1% BSA for 1 hour and visualised using anti-biotin alkaline phosphatase (1:2000 in NaPBS, 0.1% BSA) and the BCIP/NBT-AP substrate kit (Vector Labs).

Following dot blots, hybridisation with EFRU-F2 probe was carried out on sections at 46° C. for 3 hours, in hybridisation buffer, containing 0, 5, and 10% formamide, plus a no probe control of each, in an attempt to optimise the stringency for each probe. 2×15 minute washes were carried out at 50° C. Slides with control bacteria (*E. coli*) were also used at each of the formamide concentrations, with each probe, to further check for stringency. Stolon tissue was screened on sections as this provided a more uniform basis for comparisons. Successful hybridisations were repeated on larval sections.

Results:

The dot blots indicated EFRU-F2 was specific for the Type I (*Candidatus Endoecteinascidia frumentensis*) sequence, binding only to Type I 16S rDNA and not to that of the other common types isolated from *E. turbinata* or to *E. coli* 16S rDNA, under standard hybridisation conditions see Table 3.

Same results were obtained for EFRU-R1 probe.

TABLE 3

Dot-blot hybridisation of unique 16S rRNA in situ probes

| 16S rDNA PCR product | Probes | | | |
|---|---|---|---|---|
| | Eub338 | EFRU-F2 | Type III-1 | Type 111-4 |
| Type I | X | X | X | — |
| Type III | X | — | X | X |
| Type IV | X | — | — | — |
| Type VI | X | — | X | X |
| E. coli | X | — | — | — |

Type III-4 was also specific for Type III and VI sequence, but type III-I cross-reacted with the Type I DNA under these conditions. The Type I probe tested on stolon sections bound to similar cells as those highlighted by the universal eubacterial probe EUB338, suggesting that these bacteria are the *Candidatus Endoecteinascidia frumentensis* symbiont (FIG. 6C).

In situ hybridisation of EFRU-R1 probe on dissociated bud cells showed the granular cell type previously described (FIG. 6D) together with some other cells where isolated positive elements could be observed (FIG. 6E). These figures could correspond to lightly crushed granular cells showing the cellular content. The round shaped elements are suggested to be putative Type I bacteria (*Candidatus Endoecteinascidia frumentensis*), which appear tightly packed in certain cell types.

Example 6

Electron Microscopy

Electron microscopy was carried out on mature larvae. Larvae were fixed as before, post-fixed in 1% Osmium tetroxide and embedded in Spurrs resin. The blocks were orientated so that sections were cut from the developing branchial basket area (an area potentially containing the cells of interest, as identified by in situ hybridisation) and sectioned using an LKB ultramicrotome. Sections were mounted on grids and stained using uranyl acetate and lead citrate. Observations were made using a Jeol I00S Transmission Electron Microscope.

Results:

The rods of the developing branchial basket in *E turbinata* larvae were formed by elongate support cells. These were frequently vacuolated with large, electron dense inclusions (possibly lipids). Putative cells which correlated with those observed by in situ hybridisation were identified and termed "bacteriocites" (FIG. 7). They had a very similar morphology to the other major type of coelomocytes except for the presence of putative bacteria. The bacteriocytes frequently had cytoplasmic protrusions extending from the cell surface and all appeared to be free in the coelom. In small cells the nuclei were heterochromatic and unremarkable. Mitochondria were frequently observed. There were some obvious strands of rough endoplasmic reticulum, but the cells were most notable for the high densities of what are apparently polyribosomes distributed throughout the cytoplasm. There was no obvious golgi apparatus.

The putative bacteria were rounded and approximately 1-2 microns in diameter. Their membrane structure suggests that they are gram-negative bacteria and they contain no obvious organelles (FIG. 7). The chromosomal DNA is usually well distributed and only partially condensed. The bacteria appear to be healthy, particularly in the smaller cells, with any obvious shrinkage probably the results of the fixation technique rather than any pathology. No bacteria were seen being lysed.

The invention claimed is:

1. An isolated polynucleotide comprising
   (a) a nucleotide sequence SEQ ID NO: 1 or a modification, variant or fragment thereof having at least 95% identity to SEQ ID NO: 1; or
   (b) a complement to (a);
   wherein said sequence, modification, variant, fragment thereof, or complement identifies bacteria involved in the biosynthesis of ecteinascidin compounds.

2. A polynucleotide according to claim 1 having at least 97% identity or a complement thereof.

3. A recombinant DNA comprising a polynucleotide sequence according to either claim 1 or claim 2.

4. An isolated bacterium including a polynueleotide according to claim 1.

5. An isolated bacterium according to claim 4 identified as *Candidatus Endoecteinascidia frumentensis*.

* * * * *

SEQUENCE LISTING

```
<160> NUMBER OF SEQ ID NOS: 14

<210> SEQ ID NO 1
<211> LENGTH: 1502
<212> TYPE: DNA
<213> ORGANISM: Candidatus Endoecteinascidia frumentensis

<400> SEQUENCE: 1
atgaattctg gtggcactgc ttaacacatg caagtcgaac ggtaacataa taaatgtttt      60
ttacatttat ggatgacgag tggcggacgg gtgagtaacg cgtaggaacc tacctttag     120 tgggggatag cagtgggaaa ctactggtaa taccgcatga tactttagag ttaaaactag    180
ctgaatttta tagcttgtgc taaaagacgg gcctgcgtta gattagcttg ttggtaaggt    240
aacggcttac caaggcaacg atctatagct gttctgagag gaagatcagc cacactggga    300
ctgagatacg gcccagactc ctacgggagg cagcagtggg gaatattgga caatgggcgg    360
aagcctgatc cagcaatgcc acgtgtgtga agaaggcctt cgggttgtaa agcactttta    420
ttagcgaaga agatataatg gttaagagct taatatattt gacgttagct aaagaaaaag    480
caccggctaa ctccgtgcca gcagccgcgg taatacggag ggtgcaagcg ttaatcggaa    540
ttattgggcg taaagagcct gtaggtggat aattaagtca gatgtgaaat cccaaagctt    600
aactttggaa ctgcatttga aactaattat ctagagtata gtagagggta gaggaatttc    660
cggtgtagcg gtgaaatgcg tagagatcgg aaggaacatc agtggcgaag gcgtctacct    720
gggactaaaa ctgacactga gaggcgaaag catggggagc aaacaggatt agataccctg    780
gtagtccatg ccgtaaacta tgagtactaa ctgttggaat tttaaattt tagtagtgga    840 gctaacgcaa taagtactcc gcctggggat tacggccgca aggctaaaac tcaaaggaat    900 tgacggggc ccgcacaagc ggtggagcat gtggtttaat tcgatgcaac gcgaaaaacc    960
ttacctactc ttgaaatcct tcgtacttta tagagatata aaggtgcctt tggaacgaag   1020
tgacaggtgc tgcatggctg tcgtcagctc gtgtcgtgag atgttgggtt aagtcccgta   1080
```

```
acgagcgcaa ccctttccct tagttgccag cgtgtaaaga cggggactct gagggggactg    1140 ccggtgataa accggaggaa ggcgaggacg acgtcaagtc atcatggtcc ttacgagtag    1200
ggctacacac gtgctacaat ggtatgtaca aagggaggca aaattgtaaa atctagcaaa    1260
tccccaaaag catatcttag tccggattga agtctgcaac tcgacttcat gaagttggaa    1320
tcgctagtaa tcgcgaatca gcatgtcgcg gtgaatacgt tcccgggcct tgtacacacc    1380
gcccgtcaca ccacggaagt ggaatgcacc agaagtggct aggataaccg aaaggagtcc    1440
ggtccctacg gtgtgtttcg taactggggt gaagtcgtaa caaggtagcc gtagggaact    1500
gc                                                                   1502

<210> SEQ ID NO 2
<211> LENGTH: 32
<212> TYPE: DNA
<213> ORGANISM: Artificial Sequence
<220> FEATURE:
<223> OTHER INFORMATION: EFRU-F1

<400> SEQUENCE: 2
cggtaacata ataaatgttt tttacattta tg                                   32

<210> SEQ ID NO 3
<211> LENGTH: 25
<212> TYPE: DNA
<213> ORGANISM: Artificial Sequence
<220> FEATURE:
<223> OTHER INFORMATION: EFRU-R1

<400> SEQUENCE: 3
tatgcttttg gggatttgct agatt                                           25

<210> SEQ ID NO 4
<211> LENGTH: 20
<212> TYPE: DNA
<213> ORGANISM: Artificial Sequence
<220> FEATURE:
<223> OTHER INFORMATION: EFRU-R2

<400> SEQUENCE: 4
ctttcggtta tcctagccac                                                 20

<210> SEQ ID NO 5
<211> LENGTH: 23
<212> TYPE: DNA
<213> ORGANISM: Artificial Sequence
<220> FEATURE:
<223> OTHER INFORMATION: Type III-1

<400> SEQUENCE: 5
gcaactattt ctagctgtta ttc                                             23

<210> SEQ ID NO 6
<211> LENGTH: 21
<212> TYPE: DNA
<213> ORGANISM: Artificial Sequence
<220> FEATURE:
<223> OTHER INFORMATION: Type III-4

<400> SEQUENCE: 6
agctttgcac tggatgtcaa g                                               21

<210> SEQ ID NO 7
```

```
<211> LENGTH: 18
<212> TYPE: DNA
<213> ORGANISM: Artificial Sequence
<220> FEATURE:
<223> OTHER INFORMATION: EUB338

<400> SEQUENCE: 7
gctgcctccc gtaggagt                                                18

<210> SEQ ID NO 8
<211> LENGTH: 18
<212> TYPE: DNA
<213> ORGANISM: Artificial Sequence
<220> FEATURE:
<223> OTHER INFORMATION: Non-EUB338

<400> SEQUENCE: 8
actcctacgg gaggcagc                                                18

<210> SEQ ID NO 9
<211> LENGTH: 20
<212> TYPE: DNA
<213> ORGANISM: Artificial Sequence
<220> FEATURE:
<223> OTHER INFORMATION: EUB8-f
<220> FEATURE:
<221> NAME/KEY: misc_feature
<222> LOCATION: (3)..(3)
<223> OTHER INFORMATION: N is A or G
<220> FEATURE:
<221> NAME/KEY: misc_feature
<222> LOCATION: (12)..(12)
<223> OTHER INFORMATION: N is A or C

<400> SEQUENCE: 9
agngtttgat cntggctcag                                              20

<210> SEQ ID NO 10
<211> LENGTH: 18
<212> TYPE: DNA
<213> ORGANISM: Artificial Sequence
<220> FEATURE:
<223> OTHER INFORMATION: EUB1509-r
<220> FEATURE:
<221> NAME/KEY: misc_feature
<222> LOCATION: (2)..(2)
<223> OTHER INFORMATION: N is G or T

<400> SEQUENCE: 10
gntaccttgt tacgactt                                                18

<210> SEQ ID NO 11
<211> LENGTH: 21
<212> TYPE: DNA
<213> ORGANISM: Artificial Sequence
<220> FEATURE:
<223> OTHER INFORMATION: 16S-F1
<220> FEATURE:
<221> NAME/KEY: misc_feature
<222> LOCATION: (5)..(5)
<223> OTHER INFORMATION: N is G or C
<220> FEATURE:
<221> NAME/KEY: misc_feature
<222> LOCATION: (13)..(13)
<223> OTHER INFORMATION: N is A, C, or T

<400> SEQUENCE: 11
gagantttga tcntggctcag                                             21
```

```
<210> SEQ ID NO 12
<211> LENGTH: 17
<212> TYPE: DNA
<213> ORGANISM: Artificial Sequence
<220> FEATURE:
<223> OTHER INFORMATION: 1600R

<400> SEQUENCE: 12
aaggaggtga tccagcc                                                  17

<210> SEQ ID NO 13
<211> LENGTH: 17
<212> TYPE: DNA
<213> ORGANISM: Artificial Sequence
<220> FEATURE:
<223> OTHER INFORMATION: M13/pUC-f

<400> SEQUENCE: 13
gttttcccag tcacgac                                                  17

<210> SEQ ID NO 14
<211> LENGTH: 17
<212> TYPE: DNA
<213> ORGANISM: Artificial Sequence
<220> FEATURE:
<223> OTHER INFORMATION: M13/pUC-r

<400> SEQUENCE: 14
caggaaacag ctatgac                                                  17
```